(12) United States Patent
Wechler

(10) Patent No.: US 6,638,250 B2
(45) Date of Patent: Oct. 28, 2003

(54) INDWELLING VENOUS CANNULA

(75) Inventor: Ingolf Max Wechler, Ikreny (HU)

(73) Assignee: Arrabona Medical KFT (HU)

( * ) Notice: Subject to any disclaimer, the term of this patent is extended or adjusted under 35 U.S.C. 154(b) by 295 days.

(21) Appl. No.: 09/815,303

(22) Filed: Mar. 23, 2001

(65) Prior Publication Data

US 2002/0045863 A1 Apr. 18, 2002

(30) Foreign Application Priority Data

Oct. 13, 2000 (EP) .............................................. 00122467

(51) Int. Cl.[7] .......................... A61M 5/178; A61M 5/00
(52) U.S. Cl. ...................................... 604/158; 604/257
(58) Field of Search ................................ 604/247, 257, 604/158; 137/846

(56) References Cited

U.S. PATENT DOCUMENTS

| | | |
|---|---|---|
| 3,463,159 A | 8/1969 | Heimlich |
| 5,156,596 A | 10/1992 | Balbierz et al. |
| 5,776,108 A | 7/1998 | Sheu et al. |

Primary Examiner—Henry Bennett
Assistant Examiner—Sabrina Dagostino
(74) Attorney, Agent, or Firm—Rothwell, Figg, Ernst & Manbeck, p.c.

(57) ABSTRACT

An infusion apparatus including an indwelling venous cannula with a catheter holder, a plastic catheter and a steel cannula holder with a steel cannula extending through the plastic catheter and the catheter holder, a tubular valve body made of elastomeric plastic with certain length L being disposed in a channel extending centrally through the housing of the catheter holder, and the walls of the valve body lying on and directly touching each other over certain length L, whereby certain length L, the wall thickness and the Shore hardness of the valve body are coordinated with each other so that an infusion solution can pass the valve under the effect of gravity but a reflux of the patient's blood is reliably prevented. The valve body is preferably a tubular film.

14 Claims, 5 Drawing Sheets

INDWELLING VENOUS CANNULA

The present invention relates to an infusion apparatus as customarily used in medical technology for supplying solutions or blood substitutes to a patient by infusion. Infusion apparatuses of the kind in question here consist of an indwelling venous cannula, i.e. a catheter holder with a catheter of flexible plastic such as PTFE and a steel cannula holder with a steel cannula disposed on the catheter holder, the steel cannula leading axially through the indwelling venous cannula or the catheter holder and the plastic cannula so that its tip projects at the distal end of the plastic cannula. The steel cannula holder is sealed at the end axially opposite the steel cannula with a Luer lock connection, a kind of screw cap. The Luer lock connection can be removed in order to connect an infusion tube to the steel cannula holder. A thus prepared infusion apparatus is inserted into a vein and advanced as far as possible into the punctured vein. The catheter holder is then fastened to the patient's skin by means of flexible tabs and the steel cannula holder can subsequently be withdrawn completely from the indwelling venous cannula together with the steel cannula. Only the plastic cannula connected with the catheter holder fixed outside the body remains in the vein. The infusion tube can now be connected directly to the catheter holder rather than to the steel cannula holder.

When the steel cannula is removed there is a free connection between the body vein and the interior of the indwelling cannula or the interior of the channel extending through the housing of the catheter holder. Blood can therefore escape before an infusion tube is connected to the catheter holder. The same applies of course when the infusion tube is changed.

Said escape of blood must be prevented in order both to protect the patient and to protect the caretaking staff, for example nurses and doctors. Direct blood contact must absolutely be avoided in view of a possible infection (HIV, hepatitis).

It is known to avoid such dangers by providing a check valve in the channel extending through the housing of the catheter holder. However, known check valves are constructed of many single parts, accordingly difficult to assemble and also trouble-prone (DE 38 09 127 and DE 41 37 019).

The problem underlying the invention is to provide an infusion apparatus and in particular an indwelling venous cannula which has a simple structure and can thus be produced cost-effectively. Despite the simplicity of its structure the indwelling venous cannula should reliably prevent the danger of unintentional escape of the patient's blood.

This problem is solved according to the invention by the features of independents claims 1 and 8. Especially preferred embodiments and designs of the inventive indwelling venous cannula are the object of the subclaims.

In the following some embodiments of the invention will be described by way of example with reference to the enclosed drawing, in which.

Figure 1:
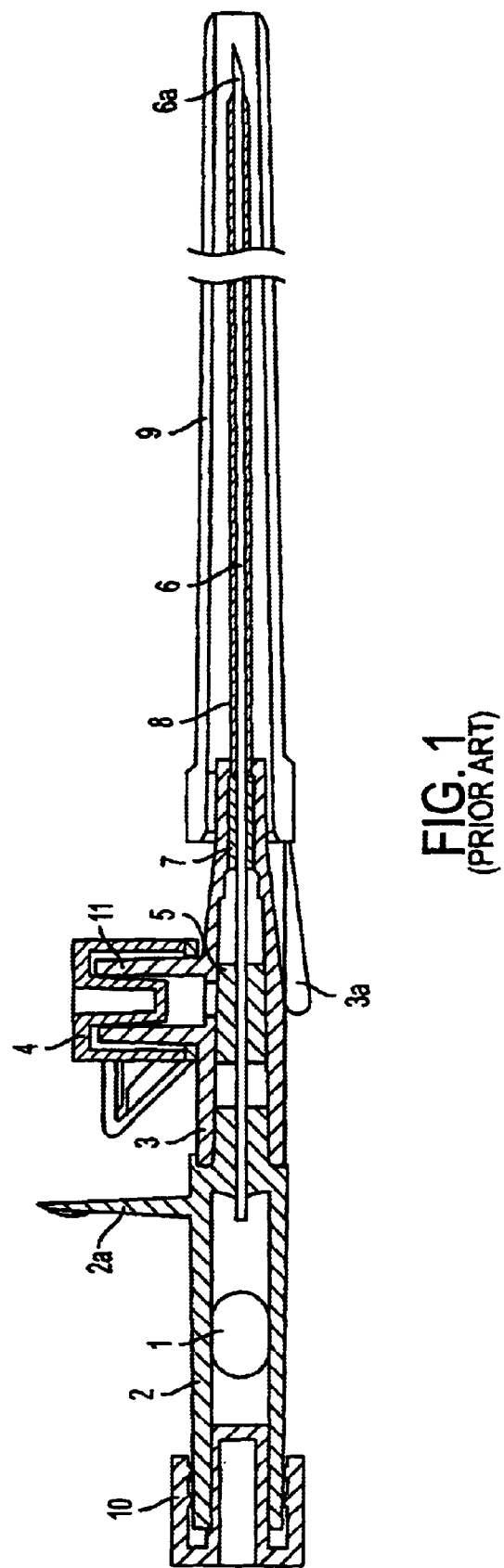
FIG. 1 shows a sectional view of a prior art infusion apparatus.

FIG. 1 schematically shows an infusion apparatus according to the prior art. The infusion apparatus consists of catheter holder 3 with plastic catheter 8, preferably made of flexible plastic such as PTFE, fastened to its right end by means of fixation sheath 7 disposed in the catheter holder. At the other axial end of catheter holder 3, steel cannula holder 2 is disposed with steel cannula 6 which extends axially completely through catheter holder 3 and plastic catheter 8 and projects from the axially opposite side of plastic catheter 8. Steel cannula holder 2 is sealed by Luer lock connection 10 on the side axially opposite steel cannula 6. Porex filter 1 is provided in steel cannula holder 2. Furthermore, steel cannula holder 2 has upward protruding attacking plate 2a which the user of the infusion apparatus can attack e.g. with the thumb in order to puncture a blood vessel with the infusion apparatus and advance the latter into the punctured vessel. The catheter holder is equipped with laterally disposed injection port 11 sealed by cap 4 in the non-used state.

Furthermore, laterally projecting flaps 3a are provided in the lower side of steel cannula holder 3 as further components thereof which rest flat on the patient's skin after puncture and can be fastened to the skin e.g. with plaster. The steel cannula with the surrounding plastic catheter is protected by cap 9 in the unused state of the infusion apparatus.

Number 5 designates a valve body which performs a valve function for radially disposed injection port 11.

Figure 2:
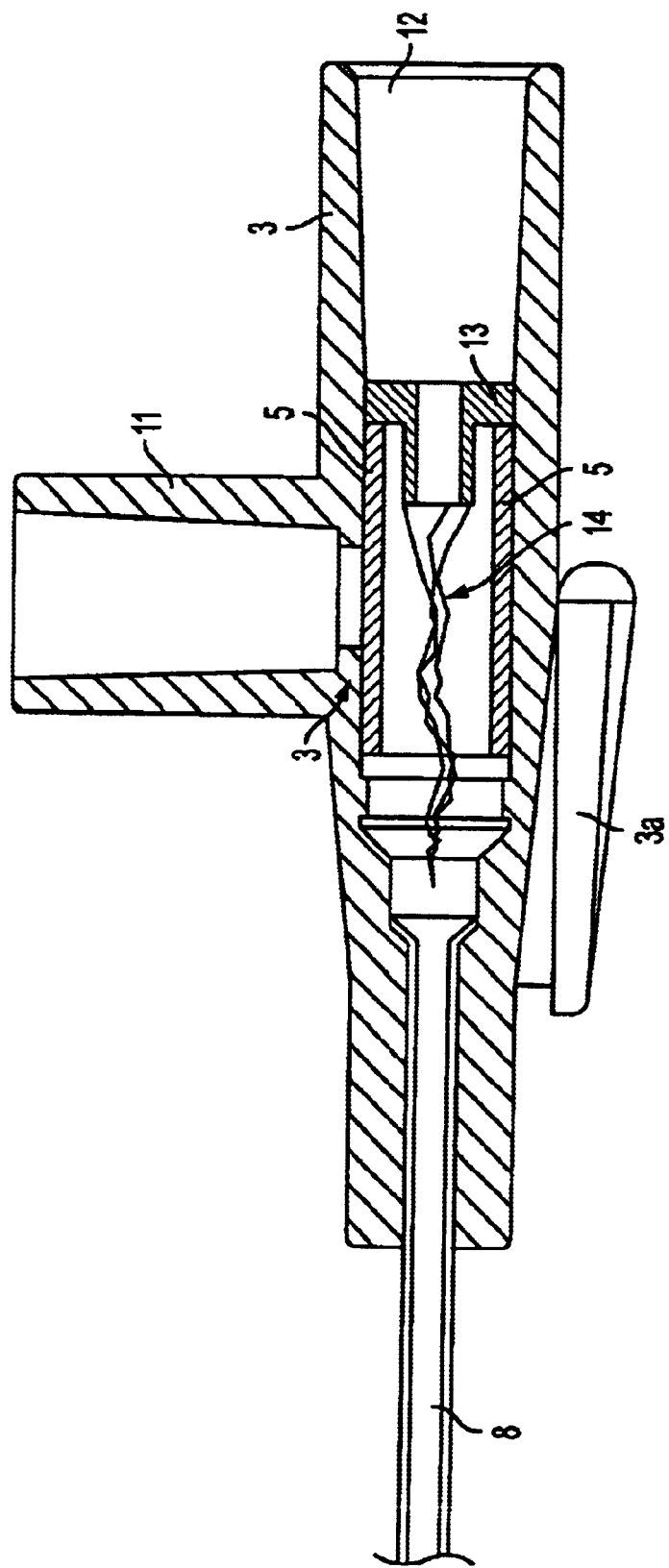
FIG. 2 shows a sectional view through a catheter holder housing according to a first embodiment of the invention.

FIG. 2 shows a first embodiment of the invention. Port 13 is sealingly inserted in channel 12 of catheter holder 3, a valve body in the form of tubular film 14 being mounted on the patient-side end of said port. The tubular film preferably consists of a thin-walled elastic material, e.g. HDPE (high density polyethylene). The length of the tubular film may be for example 10 mm, the width of the tubular film when resting flat being about 2.5 mm.

The tubular film is shown in FIG. 2 in the state which it assumes when the steel cannula is removed with the steel cannula holder from catheter holder 3. The free end of channel 12 on the right in FIG. 2 is connected with an infusion device, catheter 8 being introduced into a vein of the patient in the operative state of the apparatus. In the storage state (not shown) the steel cannula extends through the tubular film.

The infusion fluid running through the catheter holder from the right to the left penetrates tubular film 14 without difficulty. The driving pressure gradient is the differential pressure between the hydrostatic pressure of the infusion fluid and the patient's blood pressure.

It is readily evident that the tubular film can be flowed through from the right to the left but not from the left to the right. When the infusion device is detached the tubular film is instead compressed, thereby preventing any reflux. The wall thickness of the tubular film, its length and its elasticity or Shore hardness must of course be coordinated with each other so that the desired effect is obtained, i.e. that infusion fluid can penetrate the tubular film under the effect of gravity, on the one hand, but reflux of the patient's blood is reliably prevented, on the other hand. These parameters can be coordinated without any great difficulty by conducting a few tests.

Valve body 5 consists of a cylindrical sheath of elastomeric material. The sheath seals the injection opening of lateral injection port 11. When additional drugs are to be injected through said port, valve body 5 yields in the area of the passage of port 11 into housing 3 in the direction of the center axis of channel 12, releasing the path for fluid injected through said port. In the inoperative state the valve body assumes the position shown in FIG. 2, reliably sealing the outlet to injection port 11 so that no blood of the patient can escape through said port either.

Tubular film 14 can be easily slipped onto port 11. However, it may also be glued or welded by means of ultrasound.

Figure 3A:
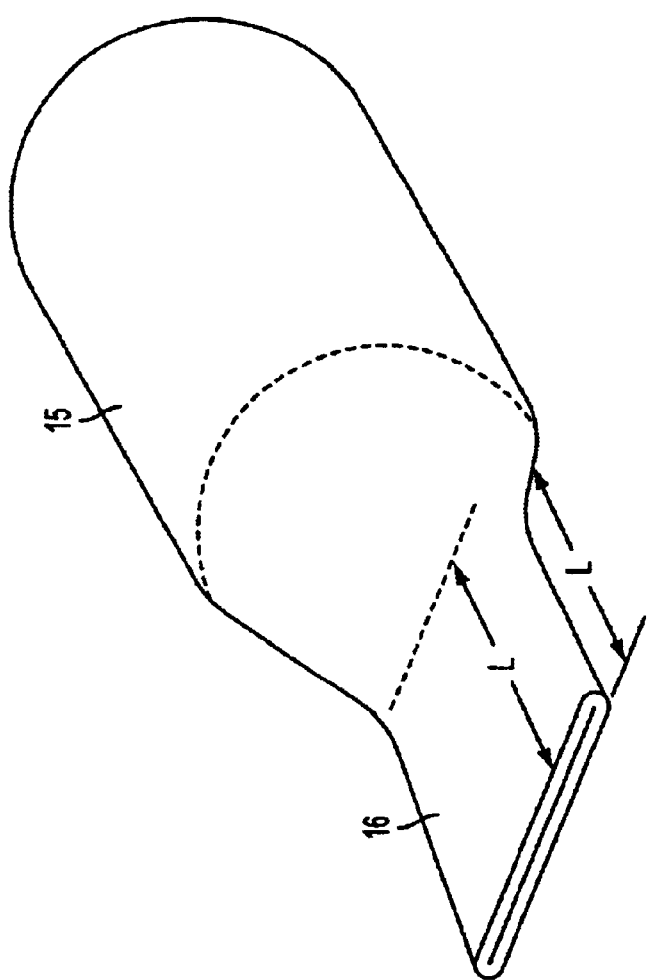
FIG. 3A shows a perspective view of a valve body according to a second embodiment of the invention.

FIG. 3A shows a perspective view of a modification of the valve body as shown in FIG. 2. Instead of tubular film 14, valve body 5 is modified so as to have, on the one hand, cylindrical area 15 which is compressed into flat area 16 on the patient side. Said flat area has certain length L. In the area of said length the walls of the valve body lie on each other, forming a kind of "duckbill."

It is readily evident that said flat area of determined length permits infusion fluid to pass from the right to the left, but no reflux of the patient's blood since the pressurized blood itself hermetically seals area 16 when the counter-pressure of the infusion fluid tends to zero.

Figure 3B:
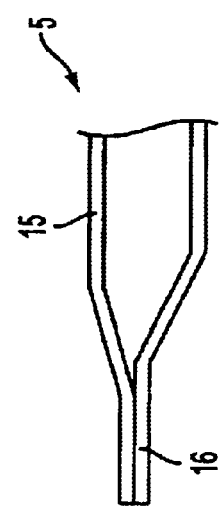
FIG. 3B shows a sectional view of the valve body shown in FIG. 3A.

Deviating from the embodiment of the invention as shown in FIG. 2, no separate tubular film is thus required here, but valve body 5, which is necessary anyway for sealing the lateral injection port, is developed as shown in FIG. 3. Thus, cylindrical area 15 of valve body 5 performs the known valve function for the lateral injection port, whereas flat area 16 with length L, the "duckbill," performs the valve function for entering infusion fluid and the blocking of reflux of patient's blood.

The valve body is preferably made of silicone, which can be readily put in a form as shown in FIG. 3 by injection molding. The wall thickness of flat area 16, and the length of flat area 16 and the Shore hardness of the material used must of course be coordinated with each other so that the described valve function is reliably fulfilled.

Figure 4A:
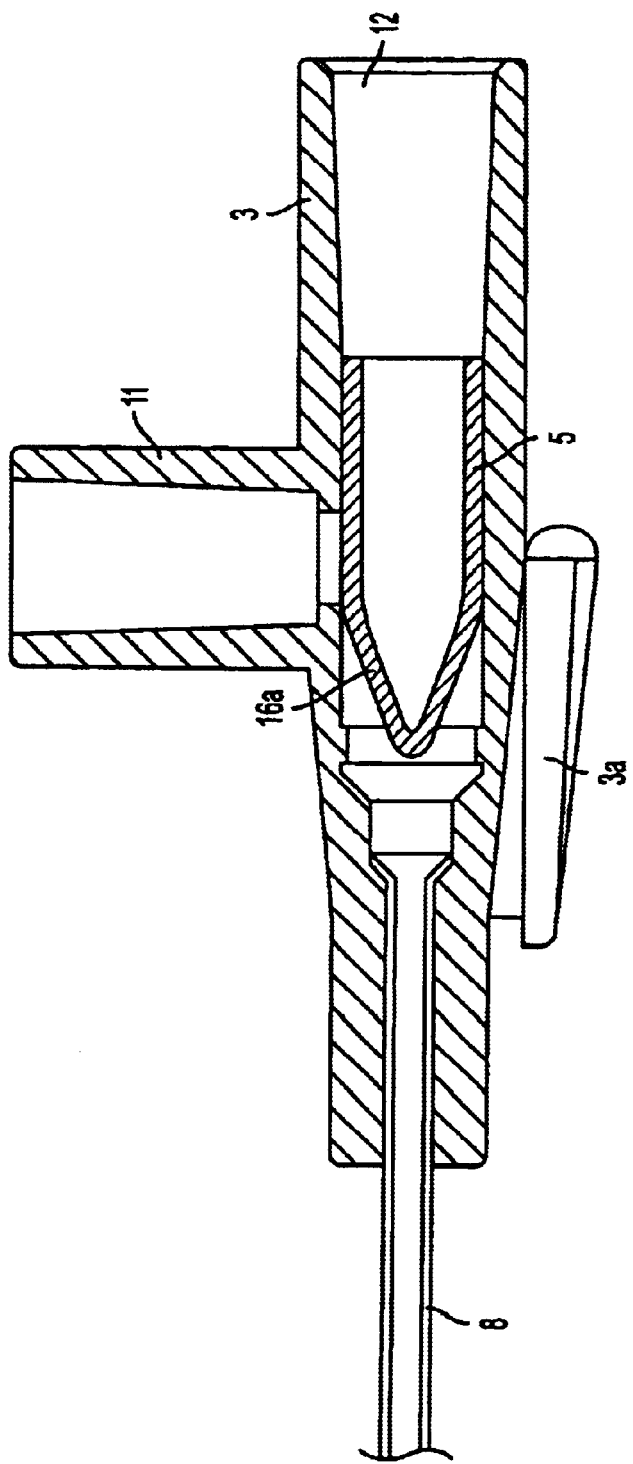
FIG. 4A shows a sectional view through a catheter holder housing according to a third embodiment of the invention.
Figure 4C:
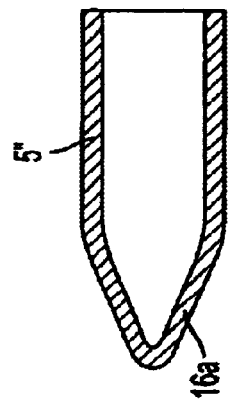
FIGS. 4B and 4C show modifications of the valve body according to FIG. 4A.
Figure 4B:
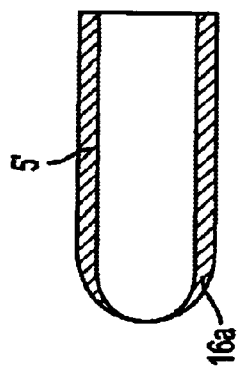

FIG. 4 shows a third embodiment of the invention wherein valve body 5 is sealed on the patient side with a cap which may be of conical or spherical form. The cap is laterally slotted starting from its apex, the slots extending substantially radially. The thus slotted caps permit the passage of infusion fluid under relatively low differential pressure, whereas reverse flow through the caps, i.e. of the patient's blood, from the right to the left in the figure, is impossible, or requires much higher differential pressure, which is not present in practice. The wall thicknesses of the material, its Shore hardness and the arrangement of the slots must of course be selected such that the desired effect is obtained. As the valve body shown in FIG. 4B shows, the wall thicknesses can also be reduced in the area of the cap. FIG. 4C again shows the valve body shown in the installed state in FIG. 4A. The cap of said valve body is conical or else tapers in the manner of a ridge prism. As in the embodiment according to FIG. 3, the valve body shown in FIG. 4 is preferably made of silicone by injection molding.

Figure 5A:
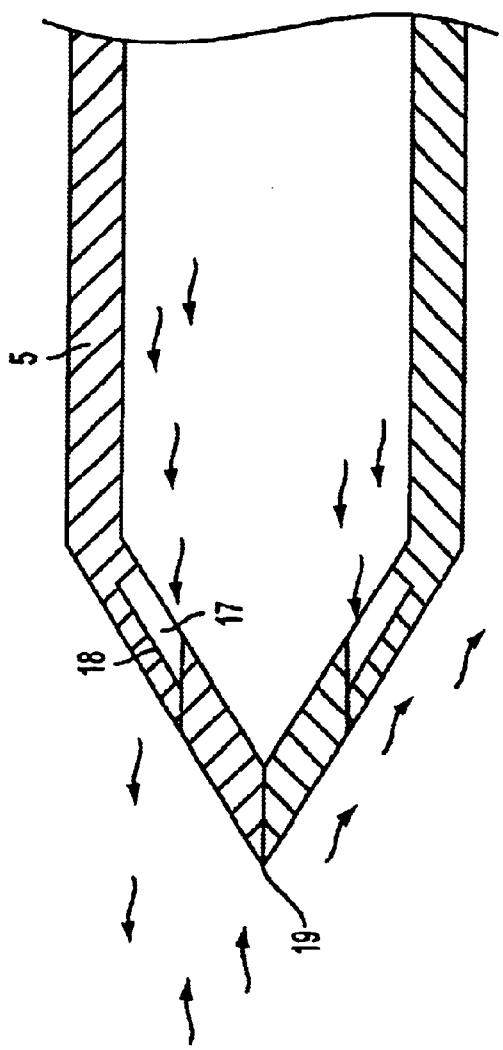
FIG. 5A shows a sectional view through a further modification of the valve body according to a fourth embodiment of the invention.
Figure 5B:
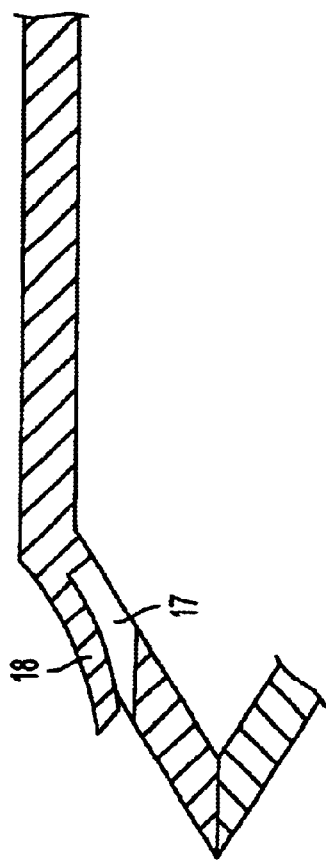
FIG. 5B shows the valve body according to FIG. 5A with a tab opened for issuing infusion solution.

FIG. 5 shows a modification of valve body 5 explained in connection with FIG. 4. The valve body shown in FIG. 5 has a relatively great wall thickness and an end cap tapering in the manner of a ridge prism to an apex which is slotted for passage of the steel cannula. This slot does not constitute a valve within the meaning of the invention, i.e. it no longer serves to pass infusion fluid after removal of the steel cannula but is hermetically sealed under relatively high closing pressure. Passage of infusion fluid takes place through window openings 17 punched into the end cap and closed by flaps 18. Flaps 18 are preferably designed with reduced wall thickness so that they can open easily, as shown schematically in FIG. 5B.

After removal of the steel cannula, central slot 19 of cap 16a will thus be hermetically sealed. The high closing force of this passage is advantageous insofar as the infusion apparatus must often be stored for long time periods with the steel cannula introduced. The long storage time readily leads to material fatigue, i.e. reduction of the elasticity and thus restoring force of the valve. In this embodiment, however, one can use such high restoring forces that slot 19 is reliably closed in any case.

The passage of infusion fluid from the right to the left in FIG. 5 is indicated by arrows and takes place through flaps 18 opening easily on the patient side. Conversely, reflux of the patient's blood presses flaps 18 firmly into window openings 17 and closes them, reliably preventing a passage of blood through the valve.

The desired valve function must of course also be optimized in this embodiment by coordinating wall thickness, design and Shore hardness of the material.

It is obvious that cap 16a of valve body 5 can also be designed in a hemispheric or conical shape instead of as the ridge prism shown in FIG. 5. As in the other embodiments, the valve body of this embodiment can be made of silicone by injection molding. Window openings 17 and the reduced wall thickness of flaps 18 are preferably produced subsequently by punching and cutting or milling.

Summing up, the invention offers an astonishingly simple solution for a check valve which works perfectly despite a long storage time with the steel cannula introduced, i.e. in the open state.

What is claimed is:

1. An infusion apparatus comprising an indwelling venous cannula with a catheter holder (3), a plastic catheter (8) and a steel cannula holder (2) with a steel cannula (6) extending through the plastic catheter (8) and the catheter holder (3), a tubular valve body (14, 15) made of elastomeric plastic with certain length L being disposed in a channel (12) extending centrally through the housing of the catheter holder (3), and the walls of the valve body (14, 15) lying on and directly touching each other over certain length L, whereby certain length L, the wall thickness and the Shore hardness of the valve body (5) are coordinated with each other so that an infusion solution can pass the valve under the effect of gravity but a reflux of the patient's blood is reliably prevented.

2. An infusion apparatus according to claim 1, wherein the valve body (5) is mounted on the patient-side end of a tubular port (13) inserted into the channel (12) of the catheter holder (3).

3. An infusion apparatus according to claim 2, wherein the valve body (5) is a tubular film (14).

4. An infusion apparatus according to claim 3, wherein the tubular film is made of HDPE.

5. An infusion apparatus according to claim 3, wherein the tubular film (14) has a width of 2.5 mm and a length of about 10 mm in the collapsed state.

6. An infusion apparatus according to claim 1, wherein the valve body (5) has a self-supporting cylindrical area (15) which is sealingly inserted into the channel (12) extending through the catheter holder (3), and the cylindrical area passes on the patient side into a flat area (16) of certain length L in which the walls lie on each other, this area providing the valve function.

7. An infusion apparatus according to claim 6, wherein the wall thickness is smaller in the flat area (16) than in the cylindrical area (15).

8. An infusion apparatus comprising an indwelling venous cannula with a catheter holder (3), a plastic catheter (8) and a steel cannula holder (2), a self-supporting sheathlike valve body (5) made of elastomeric plastic being inserted sealingly in a channel (12) extending centrally through the housing of the catheter holder (3), said valve body having at the patient-side end an end cap (16a) having at least one slot, the wall thickness, Shore hardness and axial length of the slots being coordinated with each other such that an infusion solution can pass the valve under the effect of gravity but a reflux of the patient's blood is reliably prevented.

9. An infusion apparatus according to claim 1, wherein the valve body (5) serves in its cylindrical area (15) as a valve for a radially disposed injection port (11).

10. An infusion apparatus according to claim 8, wherein the cap (16a) is spherical or conical and the slots are disposed substantially radially starting from its apex.

11. An infusion apparatus according to claim 8, wherein window openings (17) are partly punched free in the end cap (16a) which are closed by flaps (18) opening in the direction of the patient, whereby the window shape, the wall thickness of the flaps (18) and the Shore hardness of the cap material are coordinated with each other so that an infusion solution can pass the window openings under the effect of gravity but a reflux of the patient's blood is reliably prevented.

12. An infusion apparatus according to claim 11, wherein the end cap (16a) has besides the windows (17) only one central slot (19) which is for passage of the steel cannula (6) and which closes again after removal of the steel cannula (6) and performs no further valve function.

13. An infusion apparatus according to claim 6, wherein the valve body (5) is a made of silicone.

14. An infusion apparatus according to claim 3, wherein the valve body is an injection molded part.

* * * * *